Figure 1:
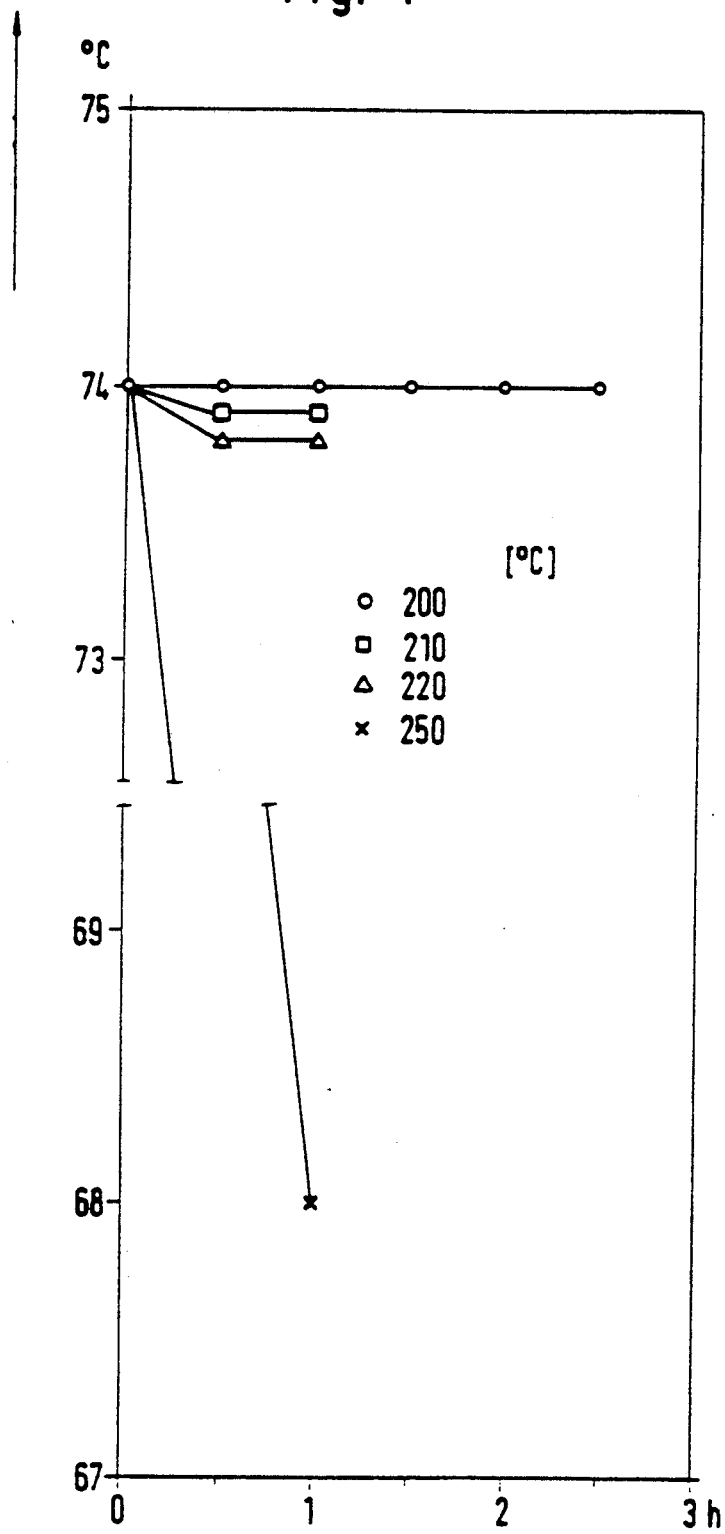

United States Patent [19]

Rittner et al.

[11] Patent Number: 5,271,811
[45] Date of Patent: Dec. 21, 1993

[54] PROCESS FOR PURIFYING 2-(4-ISOBUTYLPHENYL)-PROPIONIC ACID BY VACUUM DISTILLATION

[75] Inventors: Siegbert Rittner, Morfelden-Walldorf; Adolf Schmidt, Hofheim, both of Fed. Rep. of Germany; Larry O. Wheeler, Corpus Christi, Tex.; Gary L. Moss, Corpus Christi, Tex.; Edward G. Zey, Corpus Christi, Tex.

[73] Assignee: Hoechst Celanese Corporation, Somerville, N.J.

[21] Appl. No.: 15,270

[22] Filed: Feb. 8, 1993

Related U.S. Application Data

[63] Continuation of Ser. No. 604,383, Oct. 24, 1990, abandoned, which is a continuation of Ser. No. 302,696, Jan. 27, 1989, abandoned.

[30] Foreign Application Priority Data

Jan. 29, 1988 [DE] Fed. Rep. of Germany ....... 3802619

[51] Int. Cl.[5] .......................... B01D 3/10; C07C 51/44
[52] U.S. Cl. ......................................... 203/48; 203/49; 203/72; 203/73; 203/89; 203/91
[58] Field of Search ...................... 203/89, 91, 48, 72, 203/73, 49; 202/158; 562/406, 494

[56] References Cited

U.S. PATENT DOCUMENTS

| | | | |
|---|---|---|---|
| 3,845,121 | 10/1974 | Eubanks et al. | 562/406 |
| 4,450,047 | 5/1984 | Malzahn | 203/89 |
| 4,655,879 | 4/1987 | Brockman et al. | 203/89 |
| 4,814,494 | 3/1989 | Shimizu et al. | 562/494 |
| 4,842,696 | 6/1989 | Cazares | 203/49 |
| 4,843,172 | 6/1989 | Tanaka et al. | 562/406 |

FOREIGN PATENT DOCUMENTS

| | | | |
|---|---|---|---|
| 62-242641 | 10/1987 | Japan | 562/406 |
| 62-263140 | 11/1987 | Japan | 562/406 |
| 62-229637 | 12/1987 | Japan | 562/494 |

Primary Examiner—Wilbur Bascomb, Jr.
Attorney, Agent, or Firm—James J. Mullen; Donald R. Cassady

[57] ABSTRACT

2-(4-Isobutylphenyl)-propionic acid is purified by subjecting it to a vacuum rectification, in which the temperature is below the decomposition temperature of the acid.

26 Claims, 4 Drawing Sheets

PROCESS FOR PURIFYING 2-(4-ISOBUTYLPHENYL)-PROPIONIC ACID BY VACUUM DISTILLATION

This is a continuation of copending application Ser. No. 07/604,383 filed on Oct. 24, 1990 now abandoned, which is a continuation of Ser. No. 07/302,696 filed on Jan. 27, 1989 (now abandoned).

DESCRIPTION

The present invention relates to a process for purifying 2-(4-isobutylphenyl)-propionic acid (called 2,4-acid in the following text). The said compound is widely used, for example as an analgesic, as an anti-inflammatory agent or antirheumatic, and as an intermediate for many further substances. In the form of amine salts, aqueous solutions of 2,4-acid show good anti-corrosive behavior in metal cutting.

There are numerous possibilities for synthesizing 2,4-acid. One possibility (method A) of preparing the compound is the carbonylation of 1-(4-isobutylphenyl)-ethanol with carbon monoxide in the presence of triphenylphosphine and, if appropriate, in the presence of a transition metal halide, as is described, for example, in U.S. patent application Ser. No. 28,514, now abandoned. With optimized process operation, the resulting reaction mixture, which has to be purified, contains about 85% to 93% of 2,4-acid. In addition to 2,4-acid, the reaction mixture also contains about 40 organic impurities as well as triphenylphosphine and triphenylphosphine oxide. In order to obtain a purified 2,4-acid, which can be used as a pharmaceutical, from this reaction mixture which melts between 65° C. and 70° C., the organic impurities on the one hand and the triphenylphosphine and triphenylphosphine oxide on the other hand must be separated off or reduced to an acceptable quantity, and the concentration of triphenylphosphine and triphenylphosphine oxide in the purified product should be less than 10 ppm.

Just the separation of organic by-products from a 2,4-acid reaction mixture without triphenylphosphine and triphenylphosphine oxide is already very expensive and requires several pro-cess steps, as is evident from Romanian Patent 79,345. Thus, for example, the 2,4-acid must first be converted into a water-soluble salt, for example converted with sodium hydroxide solution into the sodium salt, the lat-ter must be freed of neutral substances by extraction with methylene chloride, the aqueous raffinate solution must be decolorized with carbon, the carboxylic acid must then be liberated with a suitable acid, i.e. hydrochloric acid, and finally recrystallized from water/methanol and dried.

In another patent specification (British Patent 971,700), it is described that the 2,4-acid from a reaction mixture is in the pure form only after having been recrystallized 3 times. Even in a more recent, very involved process, such as described in EP-A 170,147, recrystallization is chosen as the purification method for 2,4-acid.

The separation problem becomes particularly acute if—such as, for example, in method A described above—triphenylphosphine is present in the reaction mixture. As a base, triphenylphosphine forms, with the 2,4-acid and other acids in the reaction mixture, an adduct, which is stable at room temperature, of the type of the following formula

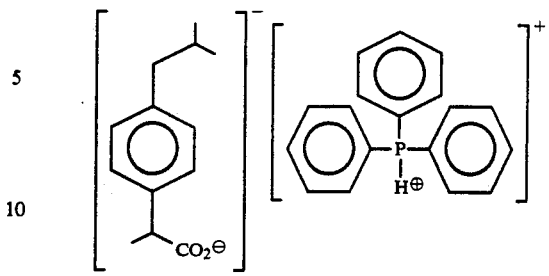

which—as our experiments showed—cannot be separated off by extraction or by repeated recrystallization from solvents (see comparison example). Other separation processes, such as adsorption on resins or ion exchangers, also do not fulfil the aim of adequately separating off all the impurities.

In the search for a suitable separation process for purifying reaction mixtures for isolating 2,4-acid, it has now been found that this object can be achieved by a vacuum rectification. This is extremely surprising because, until the said object was achieved by the present invention, purification of 2,4-acid, which melts at 74.8° C., by distillation or rectification was evidently regarded as not feasible. Neither vapor pressure data nor the boiling point of the oily-viscous liquid acid, existing above the melting point of 74.8° C., are known from the literature. The relatively high melting point of the acid makes it understandable that the chances for purification were mainly sought in crystallization from various solvents and—in the absence of triphenylphosphine—were indeed found as described, for example, in the abovementioned patent specifications. Moreover, due to the instability of 2,4-acid at high temperatures, purification by rectification evidently appeared to be a priori not very promising, in particular since other reactive components such as triphenylphosphine, triphenylphosphine oxide, ketones, styrene derivatives, alcohols and bases, which cause a deep-block discoloration going as far as the formation of tar or resinification of the mixture, can also be present in the crude acid mixture. Not last, it was also to be expected in addition that 2,4-acid forms azeotropic mixtures with one or more organic impurities.

Accordingly, the invention relates to a process for purifying 2-(4-isobutylphenyl)-propionic acid from mixtures such as are obtained in the preparation of 2-(4-isobutylphenyl)-propionic acid, which comprises subjecting the mixtures to a vacuum rectification. The process according to the invention has the advantage over the processes according to the state of the art that numerous, simultaneously present impurities, and in particular also triphenylphosphine and triphenylphosphine oxide, can be removed from the 2,4-acid in a single process engineering unit operation, with virtually no effluent and no waste air arising.

Figure 2:
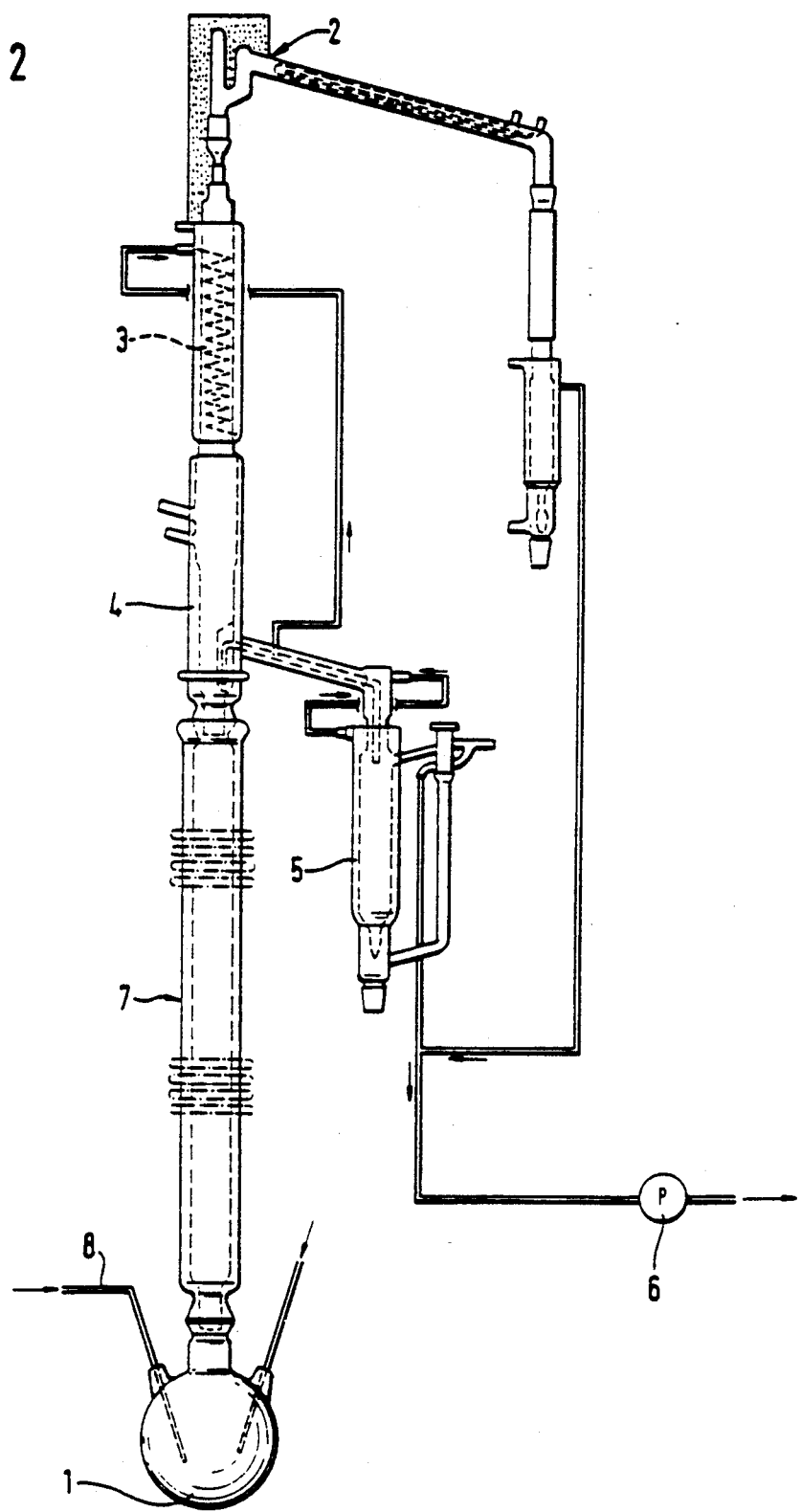

Various types of column can be employed for carrying out the process according to the invention. Columns with a metal gauze packing and columns having a pressure drop comparable to that of columns with a metal gauze packing are particularly suitable for the process according to the invention because, in these columns, the pressure drop arising is small as compared with other columns. In this connection, pressure drop means the difference between the pressure in the bottom region and in the top region of the column. A small pressure drop causes a small temperature difference between the bottom and top of a column and is necessary, because the bottom temperature in the rectification of 2,4-acid should not exceed a certain upper limit, since 2,4-acid decomposes at high temperature. The susceptibility of 2,4-acid to decomposition is illustrated by FIG. 1, in which the particular melting point—the depression of which is a measure of impurities—is plotted as a function of the duration of heating of 2,4-acid. It can be seen that, even at 250° C., the melting point of the particular sample falls already after a short heating period, which is to be ascribed to decomposition of the 2,4-acid. The susceptibility of 2,4-acid to decomposition can be further increased by impurities. For this reason, the maximum temperature, at which the process according to the invention can still reasonably be used, depends on the mixture composition. For purification of the reaction mixture arising according to method A, the bottom temperature in the rectification should therefore preferably not be above about 250° C., particularly preferably not above about 230° C. and especially not above 210° C., when a conventional rectification apparatus (still rectification apparatus) such as is illustrated, for example, in FIG. 2, is used.

When modern rectification apparatus is used, such as, for example, of the type equipped with thin-layer evaporators, or falling-film evaporators, very short residence times of the material to be rectified can be achieved, and higher bottom temperatures are thus possible in the case of such rectification apparatus, without major product losses being incurred. When the last mentioned rectification apparatus is used, the bottom temperature should preferably not exceed about 280° C.

The boiling temperature in the bottom and the vapor temperature in the region of the top of the column are given by the vapor pressure. For example at a vapor pressure of 10 hPa in the column top and 13 hPa in the bottom, the pure 2,4-acid passes over the top at 178° C. within a temperature span of 0.1° C., whereas in the bottom—due to the higher pressure and the impurities content—the boiling temperature varies between 190° and 220° C. It is advantageous to keep the vapor pressure in the bottom region at lower than about 60 hPa, so that a boiling temperature of 250° C. in the bottom is not exceeded.

The number of theoretical plates in the separation column can be varied within a wide range. A number of theoretical plates between about 10 and 150, particularly preferably between about 25 and 70, is to be preferred.

The rectification devices suitable for the purification process according to the invention can be of different structures. An example of a rectification device on the laboratory scale is shown in FIG. 2. The mixture containing the 2,4-acid is heated in the still (1) of the column. In place of the still, the device can also contain, for example, a thin-layer evaporator or falling-film evaporator. Low-boiling impurities can be distilled off at the top (2) of the column. Below the condenser, which can be, for example, a cooling coil (3) the condensate is collected in the liquid divider (4), by means of which the reflux ratio can also be adjusted. The receiver (5) in which various distillate fractions and the pure product are collected, should advantageously be controlled at a temperature of about 80° C., so that the product does not solidify. The vacuum required for the rectification is generated by suitable vacuum pumps (6). The separation column (7) is packed with a metal gauze packing and produces a separation effect of 25 theoretical separation stages as a maximum.

It is advantageous to carry out the rectification under inert gas which, in a preferred distillation device, can be introduced, for example, via a gas leak capillary tube (8) into the bottom of the column. Various inert gases are suitable for this purpose. Nitrogen, argon and carbon dioxide are preferred, and nitrogen is particularly preferred. It can also be advantageous to extract the crude 2,4-acid first with water before the rectification, in order to remove water-soluble impurities such as chlorides, phosphates, metal salts and the like.

In principle, the rectification according to the invention can be carried out by means of one or more columns either discontinuously, that is to say by taking off individual fractions, or continuously. If a continuous one-column distillation is carried out, the column can preferably be set up in such a way that the pure product is taken off as a vapor side stream approximately in the middle region of the column, while the column is preferably operated under total reflux. In continuous rectification, both the low-boiling and the high-boiling substances can first be separated off before the 2,4-acid is separated off, if for this purpose the temperature/stability limit critical for the particular reaction mixture is not exceeded.

The process according to the invention is by itself suitable for processing any possible mixtures containing synthesis of 2,4-acid, in particular those reaction mixtures which are formed in method A described above.

The process according to the invention is suitable for removing all impurities from the crude acid, arising in the production methods according to method A, without prepurification. However, it may also be appropriate to separate off only a part of the impurities by rectification and to separate off the remaining impurities by one or more purification methods. Crystallization from solvents and melt crystallization without auxiliary materials are particularly suitable for this purpose. In particular, it can be appropriate to carry out at least one melt crystallization before the rectification. In this case, the crude acid melt is converted by cooling into blocks of crystals, from which the heavily contaminated residual melt is eliminated and the crystals are subjected, after melting, to the rectification according to the invention. As a result of the said process combinations, the rectification according to the invention can be carried out with a separation column having a smaller number of theoretical plates. The invention will be explained in more detail by the illustrative examples which follow.

EXAMPLE 1

500 g of an approximately 90% 2,4-acid mixture of the following composition are employed in a fractional rectification apparatus as shown in FIG. 2.

TABLE 1

| Compound | % by weight |
| --- | --- |
| 2-(4-Isobutylphenyl)-propionic acid | 88.77 |
| Triphenylphosphine | 0.18 |
| Isobutylphenylethane | 1.90 |
| 4-Isobutylbenzene | 0.02 |
| 4-Isobutylstyrene | 0.15 |
| 4-Isobutylacetophenone | 0.78 |
| 1-(4-Isobutylphenyl)-ethanol | 0.08 |
| 1-(4-Isobutylphenyl)-chloroethane | 0.59 |
| Ethyl 2-(4-isobutylphenyl)-propionate | 0.05 |
| 2-(3-Isobutylphenyl)-propionic acid | 1.10 |
| 3-(4-Isobutylphenyl)-propionic acid | 1.90 |

TABLE 1-continued

| Compound | % by weight |
|---|---|
| Light ends of average molecular weight 178 | 1.80 |
| Heavy ends of average molecular weight 320 | 1.20 |
| Methyl ethyl ketone | 0.48 |
| Remaining unidentified impurities about | 1.0 |

Figure 3:
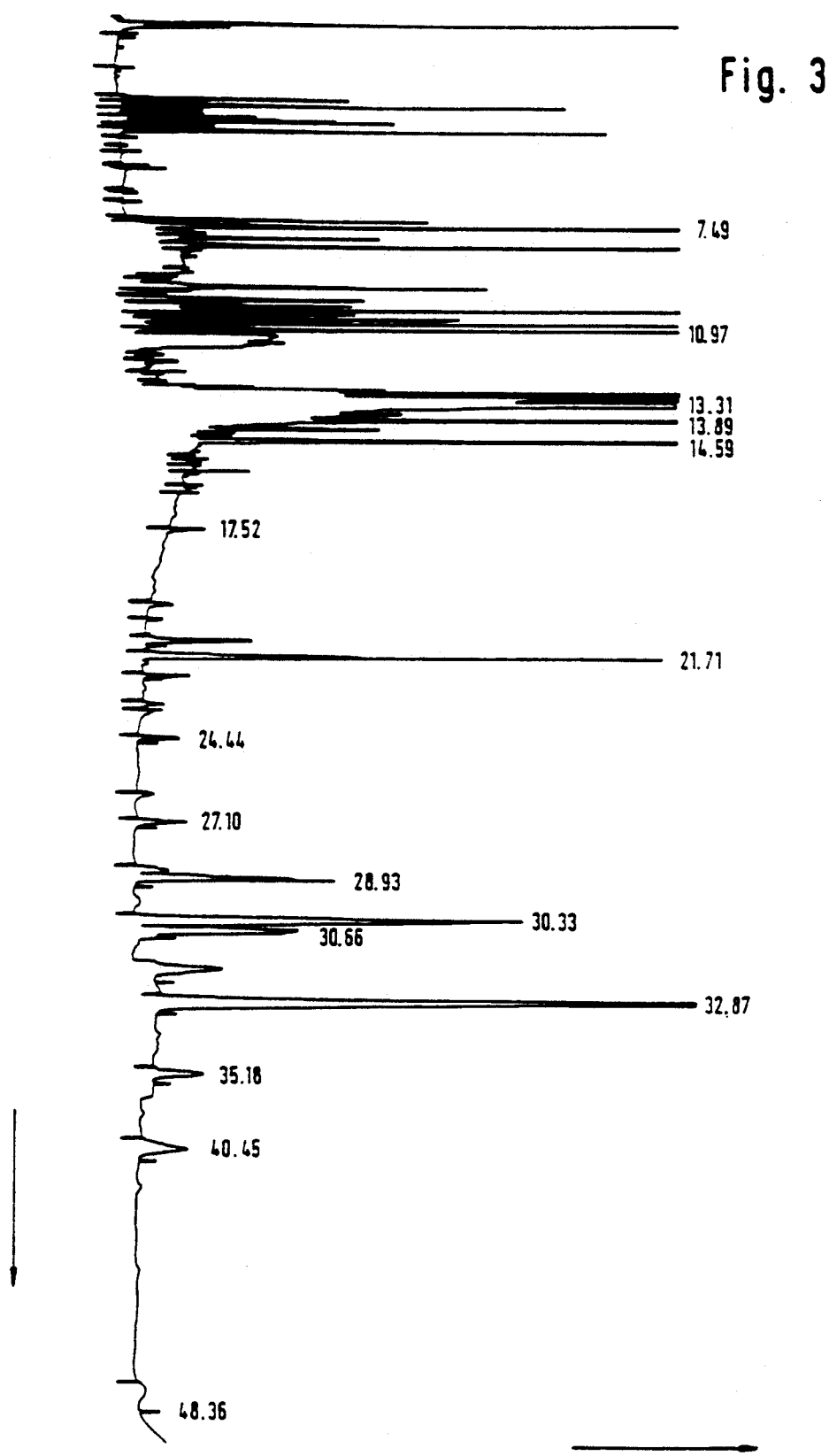

FIG. 3 shows a gas chromatogram of all the impurities in the mixture.

The mixture containing the said impurities was fractionally distilled in the presence of nitrogen under a pressure of 10 hPa and at a bottom temperature from initially 150° to finally 230° C. with varying reflux ratios. The following distillate fractions were here taken off:
1) 20 g of light ends as a yellow liquid
2) 158 g of intermediate fraction with a 2,4-acid content of 94–98%
3) 300 g of main fraction.

22 g remained as residue in the flask. The main fraction had the following composition:

| Compounds | % by weight |
|---|---|
| 2-(4-Isobutylphenyl)-propionic acid | 99.5 |
| Triphenylphosphine | 0.00005 |
| Other non-phosphororganic impurities | 0.5 |

Figure 4:
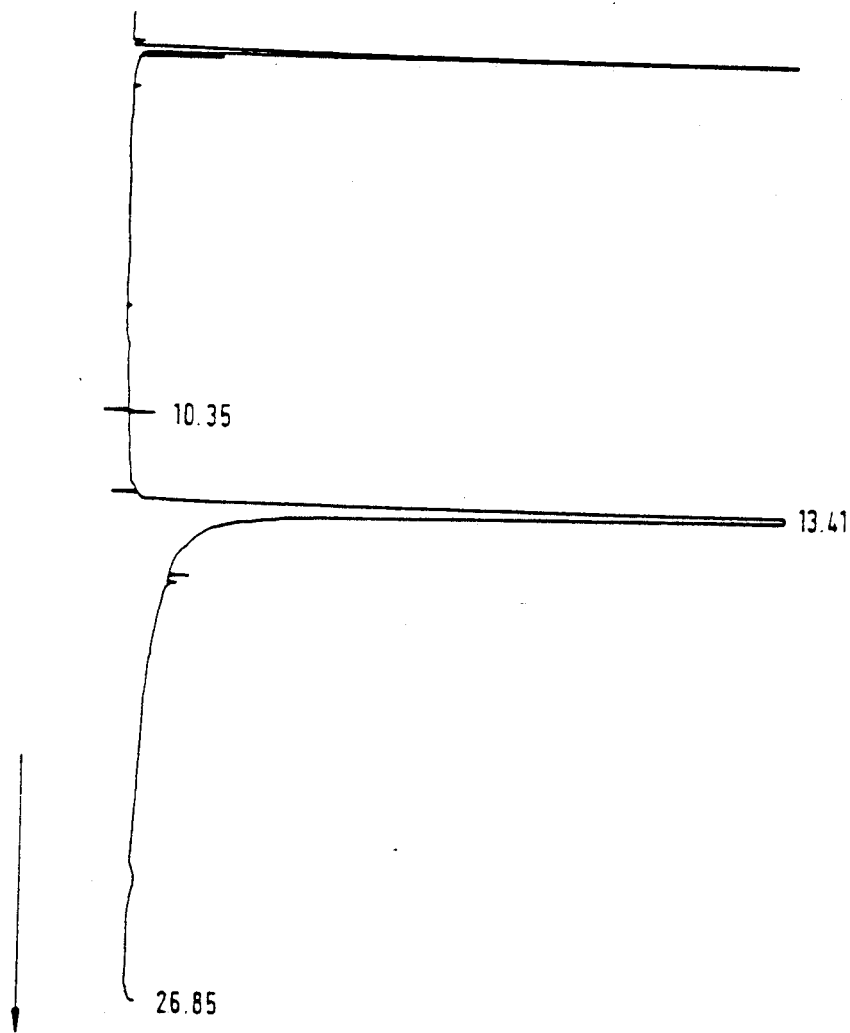

FIG. 4 shows a gas chromatogram of the main fraction.

EXAMPLE 2

Using the rectification apparatus described in Example 1, the approximately 90% 2,4-acid mixture described therein was subjected to a two-stage rectification. In this case, in the first distillation pass after the light ends have been separated off, emphasis was placed only on separating off the bottoms, in which the critical triphenylphosphine impurity concentrates. In a second rectification pass, the main fraction, containing approximately 97% of 2,4-acid, from the first rectification was rectified once more, the bottom temperature being about 200° C. In this case, the following fractions were obtained from 942 g of feed product:
1) 245 g of intermediate fraction with a 2,4-acid content of up to 98.8%
2) 640 g of main fraction
3) 57 g of distillation residue.

The main fraction had the following composition:

| Compounds | % by weight |
|---|---|
| 2-(4-Isobutylphenyl)-propionic acid | 99.5 |
| Triphenylphosphine | 0.00005 |
| Other non-phosphororganic impurities | 0.5 |

EXAMPLE 3

The approximately 90% 2,4-acid mixture of a composition as in Example 1 was introduced as a melt into a tubular crystallizer, the cooling/heating jacket of which is connected to a thermostat. The melt having a solidification point of 58° C. was cooled to 40° C. within 10 hours, compact crystals depositing in the apparatus. The dark-brown liquid fraction remaining in the crystallizer was then drained off, and the light crystals thus obtained were melted and subjected to the rectification according to the invention. 440 g of crystals having an acid purity of 98.5% were obtained from 500 g of 90% feed product.

The 2,4-acid prepurified in this way was then subjected to the rectification according to the invention up to a bottom temperature of 220° C. About 370 g of a main fraction of the following composition were obtained in this case:

| Compounds | % by weight |
|---|---|
| 2-(4-Isobutylphenyl)-propionic acid | 99.6 |
| Triphenylphosphine | 0.00005 |
| Other non-phosphororganic impurities | 0.4 |

COMPARISON EXAMPLE 1

20 g of 2,4-acid, which contained 0.4% of triphenylphosphine, were dissolved in 50 ml of n-hexane at the reflux temperature of the solvent in a 250 ml glass flask with reflux condenser. The solution was then cooled to room temperature, and the acid which had precipitated was filtered off, washed with 20 ml of cold n-hexane and dried in an exsiccator. Analysis of the recrystallized acid showed that the triphenylphosphine content had remained unchanged. The 2,4-acid thus obtained was then recrytsallized again for a second, third and fourth time from n-hexane, without it being possible to change the triphenylphosphine content.

We claim:
1. A process for isolating 2-(4-isobutylphenyl)-propionic acid from a mixture obtained in the preparation of 2-(4-isobutylphenyl)-propionic acid, said mixture comprising trivalent phosphorus compounds and halides, said process comprising rectification of said mixture in vacuum to produce a distillate containing a main fraction, such that a main fraction of the distillate substantially contains said 2-(4-isobutylphenyl)-propionic acid with not more than ten (10) parts per million of said trivalent phosphorus compound, wherein the temperature of said mixture during the rectification does not exceed about 280° C.

2. The process of claim 1 wherein the rectification is carried out by means of columns provided with metal gauze packing or columns having a comparably small pressure drop.

3. The process of claim 1 wherein the rectification is carried out using a still rectification apparatus at bottom temperatures below about 250° C.

4. The process of claim 2 wherein the rectification is carried out using a still rectification apparatus at bottom temperatures below about 250° C.

5. The process of claim 1 wherein the rectification is carried out using a rectification apparatus fitted with a thin-layer evaporator or falling-film evaporator at bottom temperatures below about 280° C.

6. The process of claim 2 wherein the rectification is carried out using a rectification apparatus fitted with a thin-layer evaporator or falling-film evaporator at bottom temperatures below about 280° C.

7. The process of claim 2 wherein the number of theoretical plates in each column is between about 10 and 150.

8. The process of claim 2 wherein the number of theoretical plates in each column is between about 25 and 70.

9. The process of claim 3 wherein the number of theoretical plates in each column is between about 10 and 150.

10. The process of claim 4 wherein the number of theoretical plates in each column is between about 10 and 150.

11. The process of claim 1 wherein the rectification is carried out in the presence of an inert gas.

12. The process of claim 1 wherein the rectification is carried out discontinuously, using one or more columns.

13. The process of claim 2 wherein the rectification is carried out discontinuously, using one or more columns.

14. The process of claim 1 wherein the rectification is carried out continuously, using one or more columns.

15. The process of claim 2 wherein the rectification is carried out continuously, using one or more columns.

16. The process of claim 1 wherein said mixture is partially purified by at least one melt crystallization prior to said rectification.

17. The process of claim 1 wherein said main fraction of the distillate is further purified using crystallization from solvents and/or melt crystallization.

18. The process of claim 1 wherein said mixture additionally contains at least trace residual amounts of a transition metal which had been used in the preparation of 2-(4-isobutylphenyl)-propionic acid.

19. The process of claim 18 wherein the rectification is carried out using a still rectification apparatus at bottom temperatures below about 250° C.

20. The process of claim 18 wherein the rectification apparatus is fitted with a thin-layer evaporator or falling-film evaporator, whereby a very short residence time is achieved, and wherein the rectification apparatus bottom temperature is below about 280° C.

21. The process of claim 19 wherein the rectification is carried out in the presence of an inert gas.

22. The process of claim 20 wherein the rectification is carried out in the presence of an inert gas.

23. The process of claim 18 wherein the rectification is carried out discontinuously using one or more columns.

24. The process of claim 18 wherein the rectification is carried out continuously using one or more columns.

25. A process for isolating 2-(4-isobutylphenyl)-propionic acid from a mixture obtained in the preparation of 2-(4-isobutylphenyl)-propionic acid, said mixture comprising trivalent phosphorus compounds and halides, said process comprising rectification of said mixture in vacuum to produce a distillate containing a main fraction, such that said main fraction of the distillate substantially contains said 2-(4-isobutylphenyl)-propionic acid with not more than ten (10) parts per million of said trivalent phosphorus compound, wherein the temperature of said mixture during the rectification does not exceed about 280° C., and wherein said mixture is partially purified by at least one (1) melt crystallization prior to said rectification.

26. The process of claim 25 wherein said mixture additionally contains at least trace residual amounts of a transition metal which had been used in the production of the 2-(4-isobutylphenyl)-propionic acid.

* * * * *